(12) United States Patent
Jendrisak et al.

(10) Patent No.: US 7,138,267 B1
(45) Date of Patent: Nov. 21, 2006

(54) METHODS AND COMPOSITIONS FOR AMPLIFYING DNA CLONE COPY NUMBER

(75) Inventors: Jerome J. Jendrisak, Madison, WI (US); Leslie M. Hoffman, Madison, WI (US); Michael J. Fiandt, Cambridge, WI (US); Darin Haskins, Madison, WI (US)

(73) Assignee: Epicentre Technologies Corporation, Madison, WI (US)

( * ) Notice: Subject to any disclaimer, the term of this patent is extended or adjusted under 35 U.S.C. 154(b) by 315 days.

(21) Appl. No.: 10/116,886

(22) Filed: Apr. 4, 2002

Related U.S. Application Data

(60) Provisional application No. 60/281,624, filed on Apr. 4, 2001.

(51) Int. Cl.
*C12N 1/21* (2006.01)
*C12N 15/63* (2006.01)

(52) U.S. Cl. .................. 435/252.3; 435/471
(58) Field of Classification Search ............ 536/23.1; 435/252.3, 473, 252.33
See application file for complete search history.

(56) References Cited

U.S. PATENT DOCUMENTS

| | | | |
|---|---|---|---|
| 5,028,530 A * | 7/1991 | Lai et al. .................. | 435/69.1 |
| 5,733,744 A | 3/1998 | Hamilton | |
| 5,874,259 A | 2/1999 | Szybalski | |
| 5,948,622 A * | 9/1999 | Reznikoff et al. ............ | 435/6 |
| 5,977,439 A | 11/1999 | Hamilton | |
| 6,022,716 A | 2/2000 | Chumakov et al. | |
| 6,030,807 A | 2/2000 | De Lencastre et al. | |
| 6,143,530 A | 11/2000 | Crouzet et al. | |
| 6,159,736 A * | 12/2000 | Reznikoff et al. .......... | 435/455 |
| 6,258,565 B1 | 7/2001 | Blatny et al. | |
| 6,258,571 B1 | 7/2001 | Chumakov et al. | |
| 6,274,369 B1 | 8/2001 | Donahue, Jr. et al. | |
| 6,294,385 B1 | 9/2001 | Goryshin et al. | |
| 6,326,350 B1 | 12/2001 | Jacobs et al. | |
| 6,346,655 B1 * | 2/2002 | Hohn et al. ................. | 800/279 |
| 2001/0046698 A1 | 11/2001 | Donahue, Jr., et al. | |
| 2002/0094575 A1 * | 7/2002 | Suzuki ....................... | 435/455 |

FOREIGN PATENT DOCUMENTS

| | | |
|---|---|---|
| WO | WO99/61034 A1 | 12/1999 |
| WO | WO00/55346 A2 | 9/2000 |
| WO | WO02/08431 A1 | 1/2002 |

OTHER PUBLICATIONS

Griffin, T.J., Parsons, L., Leschziner, DeVost, J., Derbyshire, K.M. and Grindley, N.D.F. In vitro tranposition of Tn552: tool for DNA sequencing and mutagenesis. Nucleic Acids Research, 27(19), 3859-3865 (1999).*

Merkulov, G.V. and Boeke, J.D. Libraries of green fluorescent protein fusions generated by transposition in vitro. Gene, 222, 213-222 (1998).*

U.S. Appl. No. 60/232,979.*

GeneJumper™ oriV Transposon Kit, For retrofitting BAC DNA with an oriV transposon and primer binding sites to generate high DNA yields for sequencing, Invitrogen Life Technologies, pp. 1-22, 2001. (Advertisement).

Retrofit BACs with oriV and generate high DNA yields for sequencing, Expressions 8.6, 8(6):12, 2001. (Advertisement).

M. Better, "AraB Expression System in *Escherichia coli*," Gene Expression Systems Using Nature for the Art of Expression, pp. 95-107, Academic Press, 1999.

B. Birren, et al., "Bacterial Artificial Chromosomes," Genome Analysis: A Laboratory Manual vol. 3 Cloning Systems, Cold Spring Harbor Laboratory Press, Chapter 4, pp. 241-245, 1999.

A. Blasina, et al., "Copy-up Mutants of the Plasmid RK2 Replication Initiation Protein are Defective in Coupling RK2 Replication Origins," Proc. Natl. Acad. Sci. USA 93:3559-3564, 1996.

J. M. Blatny, et al., "Improved Broad-Host-Range RK2 Vectors Useful for High and Low Regulated Gene Expression Levels in Gram-Negative Bacteria," Plasmid 38:35-51, 1997.

D. Boyd, et al., "Towards Single-Copy Gene Expression Systems making Gene Cloning Physiologically Relevant: Lambda InCh, a Simple *Escherichia coli* Plasmid-Chromosome Shuttle System," J. Bacter. 182(3):842-847, 2000.

P. K. Chatterjee, et al., "Direct Sequencing of Bacterial and P1 Artificial Chromosome-nested Deletions for Identifying Position-specific Single-nucleotide Polymorphisms," PNAS 96(23):13276-13281, 1999.

S. Choi, et al., Plant & Animal Genome VII Conference, Jan. 17-21, 1999 (Abstract).

K. S. Doran, et al., "Replication Origin of the Broad Host Range Plasmid RK2," J. Biol. Chem. 273(14):8447-8453, 1998.

R. H. Durland, et al., "Mutations in the trfA Replication Gene of the Broad-Host-Range Plasmid RK2 Result in Elevated Plasmid Copy Numbers," J. Bacter. 172(7):3859-3867, 1990.

(Continued)

*Primary Examiner*—Daniel M. Sullivan
(74) *Attorney, Agent, or Firm*—Quarles & Brady, LLP

(57) ABSTRACT

A method for retrofitting DNA in a single-copy or high-copy vector, such as a fosmid or BAC, whereby an artificial transposon is used to introduce a conditional multi-copy origin of replication ("ori") into the DNA in said vector. Following random in vitro or in vivo transposition of the ori-containing transposon into DNA in the single-copy or low-copy vector, the resulting insertion clones are introduced into a special host strain that contains a gene which encodes a polypeptide required for replication from the multi-copy ori. However, since the gene for this polypeptide is expressed from a tightly-regulated inducible promoter, the polypeptide is not expressed in the absence of inducer. On addition of inducer to the culture medium, the host cell synthesizes the polypeptide, which in turn activates replication from the multi-copy ori, thereby increasing the amount of clone DNA synthesized by the cell.

4 Claims, No Drawings

OTHER PUBLICATIONS

F. C. Fang, et al., "Mutations in the Gene Encoding the Replication-initiation Protein of Plasmid RK2 Produce Elevated Copy Numbers of RK2 Derivatives in *Escherichia coli* and Distantly Related Bacteria." Gene 133:1-8. 1993.

E. Frengen, et al., "A Modular, Positive Selection Bacterial Artificial Chromosome Vector with Multiple Cloning Sites," Genomics 58:250-253, 1999.

L. Frangeul, et al., "Cloning and Assembly Strategies in Microbial Genome Projects," Microbiology 145:2625-2634, 1999.

L. H. Hansen, et al., "Chromosomal Insertion of the Entire *Escherichia coli* Lactose Operon, into Two Strains of *Psuedomonas*, Using a Modified Mini-Tn5 Delivery System," Gene 186:167-173, 1997.

K. Haugan, et al., "The Host Range of RK2 Minimal Replicon Copy-up Mutants is Limited by Species-specific Differences in the Maximum Tolerable Copy Number," Plasmid 33:27-39, 1995.

J. J. Jendrisak, et al., "Rapid, Direct Sequencing of Bacterial Artificial Chromosome Clones using Transposomes," pp. 3-22, 2000.

P. Karunakaran, et al., "A Small Derivative of the Broad-Host-Range Plasmid RK2 which can be Switched from a Replicating to a Non-replicating State as a Response to an Externally Added Inducer," FEMS Micro. Let. 180:221-227, 1999.

A. Lamberg, et al., "Efficient Insertion Mutagenesis Strategy for Bacterial Genomes Involving Electroporation of In Vitro-assembled DNA Transposition Complexes of Bacteriophase Mu," App. Env. Micro. 68(2):705-712, 2002.

S. Perri, et al., "Interactions of Plasmid-encoded Replication Initiation Proteins with the Origin of DNA Replication in the Broad Host Range Plasmid RK2," J. Biol. Chem. 266(19):12536-12543, 1991.

M. Sektas and W. Szybalski, "Tightly Controlled Two-stage Expression Vectors Employing the Flp/FRT-mediated Inversion of Cloned Genes," Mol. Biotech. 9:17-24, 1998.

V. Shingler and C. M. Thomas, "Analysis of the trfA Region of Broad Host-range Plasmid RK2 by Transposon Mutagenesis and Identification of Polypeptide Products," J. Mol. Biol. 175:229-249, 1984.

C. A. Smith and C. M. Thomas, "Nucleotide Sequence of the trfA Gene of Broad Host-range Plasmid RK2," J. Mol. Biol. 175:251-262, 1984.

H. Shizuya, et al., "Cloning and Stable Maintenance of 300-kilobase-pair Fragments of Human DNA in *Escherichia coli* using an F-factor-based Vector," Proc. Natl. Acad. Sci. USA 89:8794-8797, 1992.

H. Shizuya and H. Kouros-Mehr, "Minireview Series for the 50th Volume, The Development and Applications of the Bacterial Artificial Chromosome Cloning System," Keio J. Med. 50(1): 26-30, 2001.

Q. Tao and H.-B. Zhang, "Cloning and Stable Maintenance of DNA Fragments over 300 kb in *Escherichia coli* with Conventional Plasmid-based Vectors," Nuc. Acids Res. 26(21):4901-4909, 1998.

J. Wild, et al., "A Broad-Host-Range in Vivo Pop-out and Amplification System for Generating Large Quantities of 50- to 100-kb Genomic Fragments for Direct DNA Sequencing," Gene 179:181-188. 1996.

J. Wild, et al., "Targeting and Retrofitting Pre-existing Libraries of Transposon Insertions with FRT and oriV Elements for In-vivo Generation of Large Quantities of any Genomic Fragment," Gene 223:55-66, 1998.

* cited by examiner

METHODS AND COMPOSITIONS FOR AMPLIFYING DNA CLONE COPY NUMBER

CROSS REFERENCE TO RELATED APPLICATONS

This application claims priority to U.S. Provisional Application No. 60/281,624 filed Apr. 4, 2001, which is hereby incorporated by reference.

STATEMENT REGARDING FEDERALLY SPONSORED RESEARCH OR DEVELOPMENT

This invention was made, in part, with United States government support award by the following agency: DOE, Grant No.: DE-FG02-00ER83003. The United States has certain rights in this invention.

BACKGROUND OF THE INVENTION

1. Field of the Invention

This invention relates to novel methods and compositions for retrofitting DNA in single-copy or low-copy vectors with the capability of replicating at higher copy number by contacting the DNA in vitro or in vivo with an artificial transposon containing a conditional multi-copy origin of replication ("ori").

2. Prior Art

Bacterial Artificial Chromosome (BAC) vectors are now widely used in sequencing projects (Roach, J C, Siegel, AF, van den Engh, G, and Hood, L. "Gaps in the Human Genome Project. Commentary, Nature 401, 843–845, 1999; Ross-McDonald, P, et al. "Large-Scale Analysis of the Yeast Genome by Transposon Tagging and Gene Disruption." Nature 402, 413–417, 1999; Mahairas, G G, et al., "Sequence-Tagged Connectors: A Sequence Approach to Mapping and Scanning the Human Genome. Proc. Nat. Acad. Sci 96: 9739–9744, 1999; Birren, B, Mancino, V, and Shizuya, H. "Bacterial Artificial Chromosomes." In: Genomic Analysis: A Laboratory Manual. Volume 3, pp. 241–295, 1999. Cold Spring Harbor Press. Cold Spring Harbor, N.Y.; Frangeul, L, Nelson, K E, Buchreiser, C, Danchin, A, Glaser, P, and Kunst, F. "Cloning and Assembly Strategies in Microbial Genome Projects." Microbiology 145, 2625–2634, 1999) because they can be used to clone and stably maintain high molecular weight DNA in *E. coli* host cells. BAC libraries containing genomic DNA inserts of up to about 300 kb are useful tools for generating sequence data. While BAC cloning has no doubt improved the ability to sequence and analyze large genomes, in certain cases BAC sequencing presents significant technical challenges. The prime remaining challenge and still a significant disadvantage of working with BAC DNA is the difficulty of obtaining adequate yields of BAC DNA from small (3 ml) cultures, a feat that is difficult at best. The low copy number of BACs (1–2 copies per host cell) yields only small quantities of DNA, which hampers sequencing projects by decreasing throughput and DNA purity compared to clones in high-copy vectors. BAC DNA can be isolated from larger amounts of culture, but this is more laborious and increases cost and time. Also, for high throughput applications, it is desirable to reduce BAC-containing culture volume below 5 ml in order to facilitate automated purification of BAC DNA. Problems encountered with BAC clones also apply to clones in fosmids and other low-copy vector cloning systems.

Inducible genes have been studied for many years and have been exploited extensively in molecular cloning processes, but have not been studied extensively as a means for at-will control of the copy number of episomal DNA in bacteria. Recently, a system was disclosed for inducing amplification of BACs (Wild, J, et al. Gene 223, 55–66, 1998; Hradecna, Z., et al., Microbial and Comp. Genomics, 3, 58, 1998; U.S. Pat. No. 5,874,259) In these disclosures, the inventors adapted a mutant version of the trfA gene product, the control element for an origin of replication called oriV from plasmid RK2, to an inducible system under the control of the araB promoter. Induction of a mutant trfA gene using the araB promoter enabled replication and amplification of BACs containing oriV.

Other inventors have used an inducible promoter, including an araB promoter, in order to express a protein which is downstream of (i.e., 3' of) the promoter on a replicable vector (E.g.s, U.S. Pat. Nos. 5,028,530; 6,242,219; and 6,274,344). However, an inducible promoter is used in the compositions and methods of the present invention to express a protein from a gene on a host chromosome and is not used to express a gene on a replicable vector.

Modifying pir-containing *E. coli* strains so that the wild-type or a mutant pir gene is under the control of an inducible promoter also offers the possibility of at-will control of episomes containing the R6Kγ ori. The R6Kγ ori was originally used for controlling the copy number of extrachromosomal elements in bacteria, depending on the strain of *E. coli* host bacteria employed (Pillarisetty, Va., et al., "The replication initiator "Pi" of plasmid R6K specifically interacts with the host-encoded helicase dnaB." Proc. Nat. Acad. Sci. (USA), 93, 5522–5526, 1996). It has found application in the construction of non-viral vectors for DNA vaccines (Suter, M, et al. "BAC-VAC, A Novel Generation of DNA Vaccines: A Bacterial Artificial Chromosome (BAC) Containing a Replication-Dependent, Packaging-Defective Virus Genome Induces Protective Immunity Against Herpes Simplex Virus 1." Proc. Nat. Acad. Sci. (USA) 96, 12697–12702, 1999). Hansen, et al. (Hansen, L H, et al. "Chromosomal Insertion of the Entire *Escherichia coli* Lactose Operon into Two Strains of *Pseudomonas*, using a Modified Mini-Tn5-Delivery System." Gene 186, 167–173, 1997) recently described the use of the R6Kγori in Tn5-based mini-transposons for moving the lac operon from *E. coli* into *Pseudomonas* species.

Recently, several laboratories have developed novel in vitro and in vivo transposon insertion systems. For example, Goryshin and Reznikoff showed that a hyperactive mutant form of Tn5 transposase catalyzes random transposition of an artificial transposon comprising almost any DNA into any other DNA in vitro so long as the artificial transposon has at its termini properly-oriented 19-basepair Mosaic End (ME) sequences that are recognized by the transposase (Goryshin, I. Y., and Reznikoff, W. S., J. Biol. Chem., 273, 7367, 1998). Further work also demonstrated that, in the absence of magnesium cations, one can make a stable synaptic complex between a hyperactive Tn5 transposase and an artificial Tn5 transposon (Goryshin, I. Y., et al., Nat. Biotechnol., 18, 97, 2000). This complex, which has been designated a "Transposome™ complex (EPICENTRE), can be electroporated into living cells, where the intracellular magnesium cations activate the transposase and generate random transposon insertions into cellular DNA in vivo. Various additional aspects of this system are disclosed in U.S. Pat. Nos. 5,925,545; 5,948,622; 5,965,443; and 6,159,736, incorporated herein by reference. Additional information is also available in the 2001 and subsequent editions of the catalog of EPICENTRE Technologies Corporation, Madison, Wis., incorporated herein by reference, and on-line at www.epicentre.com under the heading of "Transposomics™ & EZ::TN™ Transposon Tools," also incorporated herein by reference. In vitro systems have also been described for other transposons and in vitro transposon insertion kits are commercially available based on the bacteriophage Mu system (Finnzymes, Invitrogen) and on the Tn7 system (New England Biolabs, Inc.).

The advantage of using the Tn5-based Transposome™ system to deliver a R6Kγ ori rather than other Tn5-based systems is that under defined conditions, a single transposon insertion event occurs on either chromosome or extrachromosomal DNA. That is, since the artificial transposons used with Transposome™ systems or other EZ::TN™ insertion systems, as described in the 2001 and subsequent editions of the EPICENTRE catalog, do not encode a transposase gene, the inserted artificial is stable in the insertion site.

It is known that BACs exist stably in only one or two copies in host bacteria (Ross-McDonald, P., et al. "Large-Scale Analysis of the Yeast Genome by Transposon Tagging and Gene Disruption." Nature 402, 413–417, 1999; Tao, Q. and Zhang, H. "Cloning and stable maintenance of DNA fragments over 300 kb in *Escherichia coli* with conventional plasmid-based vectors." Nucleic Acids Res., 26, 4901–4909, 1998). This is an inherent disadvantage for using BACs directly as sequencing templates due to the small amount of DNA obtainable from small cultures. Tao, et al. (ibid) reported that using RK2-based plasmid vectors to increase the copy number of large clones (>300 kb) in an *E. coli* DH10B™ (Invitrogen) host permitted the maintenance of 5 to 8 copies per cell. While this system for BAC amplification appeared promising, inconsistent results were reported for cloning of human DNA.

What is Needed in the Art

What is needed in the art are improved vectors, including, but not limited to BAC, fosmid and plasmid vectors, into which DNA can be cloned and maintained in host cells at approximately one copy per host cell, but which can be induced to at least about five copies per cell on demand. Preferably, what is needed are vectors into which DNA can be cloned and maintained in host cells at approximately one copy per host cell, but which can be induced to at least about ten copies per cell. Most preferably, what is needed are vectors into which DNA can be cloned and maintained in host cells at approximately one copy per host cell, but which can be induced to at least about twenty or more copies per cell. What is needed in the art are methods that permit researchers to increase the copy number of clones in single-copy BACs, fosmids, or other low-copy vectors at will. What is needed are improved methods and vectors that permit successful cloning and stable maintenance at approximately one copy per cell of DNA comprising repetitive sequences, or AT-rich or GC-rich sequences, or sequences that are toxic or detrimental for the host cell, including without limitation, sequences that comprise one or more genes that encodes one or more peptides or proteins which is toxic or detrimental for the host cell when expressed. In short, what is needed are improved vectors that permit successful cloning and stable maintenance of difficult-to-clone sequences at approximately one copy per cell, but which can be easily and rapidly induced to higher copy number on demand.

Also needed in the art are improved *E. coli* host strains that contain a gene which encodes at least one protein required by a multi-copy ori for replication, which gene is expressed from a tightly regulated (i.e., "not leaky"), yet easily inducible transcription promoter. Preferably, under induction conditions, these improved host strains support multi-copy replication of appropriate vectors. Most preferably, under induction conditions to multi-copy replication, clones of different clone size in improved host strains yield approximately similar quantities of DNA.

Also needed in the art are compositions and methods that permit single- or low-copy vectors or clones in such single- or low-copy vectors to be easily and rapidly converted to vectors or clones which are capable of multi-copy replication following induction in a suitable host cell. What is needed are systems for using transposons to insert chemically-inducible origins of replication (ori's) in vitro and in vivo into single- or low-copy vectors or clones in such single- or low-copy vectors. What is needed are systems comprising a transposons with a multi-copy ori and an *E. coli* host strain having at least one gene that can be induced at will to express a protein that is required by the specific multi-copy ori for replication to occur. What is needed are methods for using transposon systems with inducible multi-copy ori's for facilitating sequencing. What is needed are transposon systems with inducible multi-copy ori's for retrofitting existing single-copy BAC libraries by transposon insertion in vivo or in vitro, making existing clones more amenable for automated, high throughput sequencing.

What is needed in the art are transposon systems with inducible multi-copy ori's for in vitro or in vivo insertion directly into genomic DNA. What is needed are copy-controllable systems for "rescue cloning" of genomic DNA for sequencing.

Objects of the Invention

A primary object of the present invention is to improve cloning by permitting control of clone copy number at-will. Another object of the invention is to improve sequencing, particularly high throughput sequencing, by permitting control of clone copy number at-will, most particularly by permitting control of clone copy number for clones in BAC, fosmid, and plasmid vectors.

Another primary object of the invention is to provide improved methods and vectors that permit successful cloning and stable maintenance at approximately one copy per cell of DNA comprising repetitive sequences, or AT-rich or GC-rich sequences, or sequences that are toxic or detrimental for the host cell, including without limitation, sequences that comprise one or more genes that encodes one or more peptides or proteins which is toxic or detrimental for the host cell when expressed. In short, what is needed are improved vectors that permit successful cloning and stable maintenance of difficult-to-clone sequences at approximately one copy per cell, but which can be easily and rapidly induced to higher copy number on demand.

Another primary object of the present invention is to provide improved vectors having an oriV multi-copy origin of replication in order to improve upon the invention described in U.S. Pat. No. 5,874,2590 and related patent applications, incorporated herein by reference.

Another primary object of the invention is to provide a method for using one or more artificial transposons to randomly insert an inducible multi-copy ori into clones in single-copy or low-copy vectors in vitro or in vivo. Another object of this embodiment of the invention is to generate random transposon insertion clones having primer binding sites for bidirectional sequencing of clones which are too large to sequence with a single set of sequencing reactions. Still another object of this embodiment of the invention is to eliminate the need to subclone clones larger than about one kilobase in size into smaller shatter clones for sequencing. Still another object of this embodiment of the invention is to provide a method to control clone copy number at-will at either about one copy per cell or at multiple copies per cell. An object of this embodiment is to permit stable maintenance of large clones at about one copy per cell, while permitting at-will induction to higher copy number for use in sequencing or other purposes. Another object of the invention is to provide compositions and kits comprising artificial transposons having at least one inducible multi-copy ori and, optionally having at least one selectable marker, for use in carrying out the methods of this embodiment of the invention.

Another object of the present invention is to provide a method for obtaining a suitable host strain having a gene which encodes at least one protein required for replication from the oriV origin of replication, which gene is under the control of an inducible promoter, and which host strain is an improved strain for use in the methods of the present invention and for use in the inventions described in U.S. Pat. No. 5,874,2590. Still another object of the present invention is to provide an improved $E.$ $coli$ strain which expresses a mutant form of the trfA gene product under the control of an inducible araB promoter, which strain provides improved results in the methods of the present invention and improved results for the inventions described in U.S. Pat. No. 5,874, 2590, and related patent applications by the same inventors.

Another object of the invention was to use an inducible origin of replication in concert with a Transposome™ complex to increase BAC copy number in a suitable host cell.

Another object was to develop methods for using transposons with inducible ori's, such as, but not limited to, the oriV/trfA or R6Kγ/pir systems, and BAC vector systems using either or both, depending on the results of further experiments.

Another object was to construct chemically-inducible ori's, and then to use these to make a system consisting of copy number-controllable ori-containing transposons and complementary $E.$ $coli$ strains host strains that can be induced to express different levels of an appropriate ori-specific protein. An object of this aspect of the invention was to provide a system that is useful in sequencing projects by retrofitting existing BAC libraries by transposon insertion in vivo or in vitro.

Another object was to provide inducible ori-containing transposon systems that would also be useful for in vitro insertion directly into genomic DNA or, using a Transposome™ system, for in vivo insertion and for "rescue cloning" of genomic DNA for sequencing.

A primary object of the invention was to develop systems for amplification of BAC clones in host cells to improve the yield of BAC DNA from small cultures Another primary object of the invention is to provide improved compositions of an oriV/trfA inducible system with respect to applications described elsewhere (Wild, J, Sektas, M, Hradecna, Z, and Szybalski, W. "Targeting and Retrofitting Pre-existing Libraries of Transposon Insertions with FRT and ori'V Elements for in-vivo Generation of Large Quantities of Any Genomic Fragment." Gene 223, 55–66, 1998).

Another object is to provide an inducible R6Kγ/pir system by replacing the promoter region of the pir gene from $E.$ $coli$ EC100D™ pir+ and EC100D™ pir-116 by an inducible promoter, including but not limited to, an inducible araB promoter, under the control of a simple non-metabolizable chemical using standard recombinant DNA methods.

Another primary object of the invention is to construct inducible oriV- and R6Kγ-containing transposons, BAC cloning vectors and new $E.$ $coli$ host strains for the stable maintenance of multi-copy BACs.

Another object is to construct transposons containing either the R6Kγ or oriV origins of replication by using a plasmid that is specifically designed for transposon construction, i.e., pMOD-2™ (EPICENTRE), which is a plasmid that contains a ColE1 ori (for growth in a standard cloning host), an ampicillin resistance selectable marker, the outer ends (OEs) required for use with the hyperactive Tn5 transposase, PCR priming sites for amplification of the recombinant transposon, and a multiple cloning site in between the OEs.

An object of this aspect of the invention is to construct new transposons by:

a) inserting an inducible origin of replication into the multiple cloning site of a plasmid comprising the transposon construction vector;

b) Inserting a selectable drug marker [e.g., Kan(sup)R] into said plasmid;

c) transforming the recombinant, transposon-containing plasmid into a standard cloning strain of $E.$ $coli;$ d) purifying the transposon-containing plasmid;

e) amplifying the recombinant transposon by PCR using standard methods (O'Mullan, P, "Direct Sequencing of BAC Clones Without Subcloning or Primer Walking." EPICENTRE Forum 7:4, 1–3, 2000. Published by EPICENTRE, Madison, Wis.), and f) digesting the excised transposon with restriction enzymes PvuII or PshA1, to generate precise transposon ends.

Another object is to use the resulting transposons containing oriV or R6Kγ ori to introduce the inducible origins into BACs by through in vivo insertion ("Transposome") techniques.

Another primary object of the invention is to develop new strains of $E.$ $coli$ containing an inducible regulatory gene for activating extrachromosomal origins of replication.

An object of this aspect of the invention is to construct new strains of $E.$ $coli$ carrying either the inducible pir gene or inducible $P_{araBAD}$-trfA systems, capable of inducing the function of the R6Kγ or oriV, respectively.

Another object of this aspect of the invention is to construct these new strains by using existing strains of $E.$ $coli$ containing either the $P_{araBAD}$-trfA system or inducible promoter/pir gene systems.

Another object of this aspect of the invention is that strain constructed should have the following characteristics:

1. It must contain the origin-specific regulatory gene.
2. The regulatory gene must contain a promoter that may be induced using a simple metabolic compound (such as a carbohydrate) and otherwise remain in a state permitting the stable existence of large BACs.
3. It must not have any active recombination systems, such as recABCD, which could, in some cases, permit any extrachromosomal DNA to integrate into the host chromosome by homologous recombination.
4. The new strain should be based upon existing $E.$ $coli$ strains with suitable genetic pedigrees that permit identification of suitable origins of replication and controlling host-encoded regulatory genes that function as needed.

Still another object of this aspect of the invention is that construction of the strain will be accomplished using standard recombinant DNA technologies to modify existing strains of *E. coli* containing the pir gene (both wild-type and pir-116 mutant) that have been developed for use with existing R6Kγ-containing transposons.

Another primary object of the invention is to construct new BAC vectors containing inducible origins of replications by modification of an existing BAC vector for use in constructing BAC libraries de novo.

An object of this aspect of the invention is to construct a new, inducible vector from the existing pIndigoBAC-5 vector, a derivative of pBeIoBAC and pIndigoBAC (Birren, B, Mancino, V, and Shizuya, H. "Bacterial Artificial Chromosomes." In: Genomic Analysis: A Laboratory Manual. Volume 3, pp. 241–295, 1999. Cold Spring Harbor Press, Cold Spring Harbor, N.Y.).

Another object of this aspect of the invention is to construct a new vector by modifying the pIndigoBAC vector to contain either the oriV or R6Kγ ori.

Another primary object of the invention is to amplify BAC DNA using an inducible system.

One object of this aspect of the invention is to develop a method to generate "amplified" BAC DNA in a specific *E. coli* host cell using chemical induction.

Another object of this aspect of the invention is to provide methods for BAC amplification which involve maintaining the BAC at its normal 1–2 copies per cell until growth in culture reaches mid- to late-logarithmic phase and then to introduce a chemical into the culture medium that triggers the ori-regulating gene to be expressed, thereby activating the inducible ori, and leading to replication and amplification of BAC DNA.

Another object of this aspect of the invention is to provide improved methods for BAC amplification with respect to:

1. level of amplification for different sizes of BACs
2. the time required to amplify BAC DNA in an *E. coli* host by at least 10-fold
3. the stability of the amplified BAC DNA with respect to deletions, etc A primary object of this aspect of the invention is that BACs used in the methods of the invention should lack of deletions or other recombination events in order to ensure that a single BAC species is present in a cell.

Another primary object of this aspect of the invention is that at least one of the inducible BAC systems developed can a) maintain a large (>200 kb) BAC in one or two copies until mid- to late-log phase in the host cell, and then be amplified by chemical induction to yield a minimum 10-fold increase in purified BAC DNA over what can be recovered from small cultures (3–5 ml) of a standard BAC using standard BAC DNA isolation methods, such as commercially-available BAC purification systems or standard alkaline lysis procedures (Birren, B, Mancino, V, and Shizuya, H. "Bacterial Artificial Chromosomes." In: Genomic Analysis: A Laboratory Manual. Volume 3, pp. 241–295, 1999. Cold Spring Harbor Press, Cold Spring Harbor, N.Y.).

Another primary object of the invention is to improve sequence analysis by using amplifiable BACs.

A primary object of this aspect of the invention is to adapt an inducible BAC system to large-scale, high throughput sequencing using automated procedures.

Another primary object of this invention is to develop inducible ori-containing transposons and vectors, as well as complementary *E. coli* host strains for use in systems for commercialization.

Notations and Nomenclature

The terms used herein have the following meaning with respect to the present invention:

As used herein, a "vector" is a DNA molecule in which other DNA, including, but not limited to "foreign" or "heterologous" DNA, can be operably joined so as to form a circular DNA molecule which can replicate autonomously following its introduction into a host cell. The words "foreign" or "heterologous" refer to the fact that the DNA which is operably joined to the vector is not normally present in the host cell in which it is replicated. The most common method by which the DNA is "operably joined" to a vector is by covalent joining of compatible ends by means of an enzyme referred to as a ligase, such as, but not limited to, T4 DNA ligase, by a process referred to as "ligation." The process of ligating a DNA molecule in a vector and then replicating this molecule in a host is referred to as "molecular cloning," and a product of this process is referred to as a "clone." The methods of the present invention are not limited to a particular vector or host cell, but are intended to apply to any vector and any host in which one can clone and maintain a DNA molecule at a low copy number and then, using the methods of the invention, induce the vector or its clone to a higher copy number whenever desired. By way of example, but not of limitation, a vector of the invention can be a single-copy or a low-copy BAC, fosmid, plasmid, a P1 vector, or nay other suitable vector. The host cells can be *E. coli*, or any other bacterial or other cells, including prokaryotic or eukaryotic cells, in which the vector is able to replicate at a low copy number, and which can be induced to higher copy number by means of an inducible ori according to the methods of the invention.

As used herein, the word "replicate" refers to the fact that the vector and the DNA to which it is operably joined is copied or reproduced or duplicated in the host cell by a process called "replication." The site on the vector DNA at which replication begins is referred to as the "origin of replication ("ori")." An origin of replication which requires the presence of another protein or another molecule in order for replication to occur is referred to as a "conditional origin of replication." A conditional origin of replication permits one to control replication by providing a means for controlling the expression or properties of the protein or other molecule which is required for replication from the ori. The number copies of a particular vector or of a clone in a particular vector varies based on a different factors, including, but not limit to, the sequence and structure of a particular origin of replication and the structure, amount, and properties of proteins which interact with the origin. For the purpose of the present invention, the oriV disclosed by the inventors comprises the sequence disclosed herein as SEQ. ID NO. 1 and said sequence is preferred in the methods and compositions of the invention. Examples of the present invention include the use of oriV or R6Kγori as an origin of replication, but the methods of the invention are not limited to the use of these ori's, and these same ori's can be modified to some extent to achieve the same effect. Based on the descriptions herein, those with skill in the art will know how to determine whether or not a particular ori is suitable for use in the invention and will be able to identify other ori's for use in the methods and compositions of the invention.

SEQ. ID NO. 1. Sequence of oriV

```
  1 GCTGGTTGCC CTCGCCGCTG GGCTGGCGGC CGTCTATGGC CCTGCAAACG CGCCAGAAAC

61 GCCGTCGAAG CCGTGTGCGA GACACCGCGG CCGGCCGCCG GCGTTGTGGA TACCTCGCGG

121 AAAACTTGGC CCTCACTGAC AGATGAGGGG CGGACGTTGA CACTTGAGGG GCCGACTCAC

181 CCGGCGCGGC GTTGACAGAT GAGGGGCAGG CTCGATTTCG GCCGGCGACG TGGAGCTGGC

241 CAGCCTCGCA AATCGGCGAA AACGCCTGAT TTTACGCGAG TTTCCCACAG ATGATGTGGA

301 CAAGCCTGGG GATAAGTGCC CTGCGGTATT GACACTTGAG GGGCGCGACT ACTGACAGAT

361 GAGGGGCGCG ATCCTTGACA CTTGAGGGGC AGAGTGCTGA CAGATGAGGC GCGCACCTAT

421 TGACATTTGA GGGGCTGTCC ACAGGCAGAA AATCCAGCAT TTGCAAGGGT TTCCGCCCGT

481 TTTTCGGCCA CCGCTAACCT GTCTTTTAAC CTGCTTTTAA ACCAATATTT ATAAACCTTG

541 TTTTTAACCA GGGCTGCGCC CTGTGCGCGT GACCGCGCAC GCCGAAGGGG GGTGCCCCCC

601 CTTCTCGAAC CCTCCCGG
```

The examples of the present invention also disclose the use of host cells which express either mutant or wild-type forms of the TrfA Protein, a product of a form of the trfA gene, or of the Pi Protein, a product of a form of the pir gene, as polypeptides which affect replication from oriV or from R6Kγori, respectively. However, the methods of the present invention apply to any ori which can be made conditional on the expression, and the invention can use any protein or other polypeptide or other factor which is required by or which supports an ori that can be used according to the invention in order to obtain multi-copy replication in a desired host.

Preferably, synthesis of a protein or other polypeptide required for replication from a particular ori in the host cells is tightly controlled (i.e., "not leaky"). Most preferably, the protein or polypeptide is controlled by means of an inducible transcriptional promoter that is operably joined "upstream of" or "5'-of" the gene encoding said required protein or polypeptide. A "transcriptional promoter" or more simply a "promoter" is a sequence on a DNA molecule which is recognized by an RNA polymerase enzyme and at which transcription, meaning synthesis of RNA, is initiated.

Transcription of DNA into RNA is required for synthesis and expression of the protein or polypeptide. There are a number of promoters known in the art which are suitable for the methods of the invention. By way of example, but not of limitation, the araB promoter, which can be induced by treating host cells with L-arabinose, and the Tet promoter, which can be induced by treating host cells with anhydrotetracycline (Lutz, et al., Nucleic Acids Res., 25, 1203, 1997), are preferred promoters in the invention, but there are also many other suitable promoters which can be used. Those with skill in the art will also realize that accessory proteins and the genes which encode them are sometime necessary or beneficial for use in the invention, and are envisioned under the invention. By way of example, but not of limitation, the araC sequence can be linked to an araB promoter for use in the methods and compositions of the invention. As used herein, an "inducer" is a substance that activates the promoter, either by positively regulating the transcription from the promoter, or by binding to a repressor that would otherwise inhibit transcription from the promoter. In either case, the inducer activates transcription from an inducible promoter Transcription of DNA into RNA is required for synthesis and expression of the protein or polypeptide.

A "transposable element", is a DNA sequence that can move (transpose) from one site in DNA to another.

"Transposition" is the process in which a transposable element is excised from one site and inserted into a second site on the same or another DNA molecule.

A "transposase" is an enzyme that catalyzes transposition. As used herein, the enzyme can be the wild type enzyme or a mutant form of the enzyme, which may, for example, give the enzyme a desirable property, such as, but not limited to, a higher activity. One transposase used in the present invention is a hyperactive mutant form of Tn5 transposase, which is also sometimes referred to as "EZ::TN™ Transposase" (EPICENTRE). However, the invention is not limited to this enzyme, and, unless otherwise specifically limited, other transposases are also intended to be within the scope of and covered by the invention. By way of example, but not of limitation, other transposases which can be used for the methods of the invention include Tn7 transposase, Mu transposase, Mariner transposase, Tn552 transposase (Griffin IV, T J, et al., "In vitro transposition of Tn 552: a tool for DNA sequencing and mutagenesis," Nucleic Acids Res., 27, 3859–3865, 1999), Tn10 transposase, and the like.

Traditionally, a "transposon" is defined as a transposable element that carries a gene encoding a transposase, as well as a gene or genes with other functions, such as resistance to antibiotics. However, recently Goryshin and Reznikoff (Goryshin, I Y, and Reznikoff, WS, "Tn5 in vitro transposition." J. Biol. Chem., 273, 7367, 1998) showed that purified wild type and mutant forms of Tn5 transposase can catalyze in vitro transposition of any DNA that is between two properly oriented copies of a Tn5 transposase recognition sequence, which, with respect to Tn5 transposase, is usually called an "Outer End" or an "OE" sequence or an "Inner End" or an "IE" sequence, or a "Mosaic End" or an "ME" sequence, depending on the particular transposase used, but the recognition sequence for any particular transposase which can be used for the invention can also be referred to by a different name. A particular ME sequence was identified which had optimal properties for in vitro transposition using a hyperactive form of Tn5 transposase (Zhou, M A, et al., "Molecular genetic analysis of transposase-end sequence recognition: cooperation of three adjacent base pairs in specific interaction with a mutant Tn5 transposase," J. Mol. Biol., 276, 913, 1998). In view of the findings of Goryshin and Reznikoff (Goryshin, I Y, and Reznikoff, W S, "Tn5 in vitro transposition." J. Biol. Chem., 273, 7367, 1998), it will be understood that the gene for the transposase does not need to be present in order to obtain transposition, provided that a transposase is present in a reaction mixture in which the transposase has activity. Therefore, the definition of a "transposon" as used herein, which the inventors sometimes also refer to as an "artificial" transposon, is any DNA that has recognition sequences (or OE sequences or ME sequences) for the transposase such that the DNA is capable of transposase-catalyzed transposition. As used herein, the inventors intend that all transposons of the invention do not encode an active transposase gene (meaning a transposase gene that is expressed in a host cell so as to produce an active transposase), whether or not the transposon is referred to as an "artificial" transposon. It is preferable that a transposon or artificial transposon of the invention does not encode a gene for a transposase because, in the absence of an active transposase gene, the transposon is not be able to transpose to a new location in the absence of added transposase enzyme and suitable reaction conditions.

As used herein, an "EZ::TN™ Transposon" comprises any DNA that transposes into another DNA in the presence of EZ::TN™ Transposase. Any DNA between two properly-oriented 19-basepair transposase recognition sequences or ME sequences recognized by EZ::TN Transposase can serve as an EZ::TN Transposon. A growing number of EZ::TN Transposons having different selectable markers and promoters which are active in different biological systems are available from Epicentre. Examples include EZ::TN <TET-1> Transposon and EZ::TN <KAN-2> Transposon. Alternatively, custom EZ::TN Transposons may be prepared by using a Transposon Construction Vector such as PMOD™ <MCS>, or by PCR using primers containing OE Sequences, or by ligating OE Sequences to the ends of the desired transposon DNA. Although the inventors may refer to EZ::TN Transposons herein, the invention is not limited to these transposons and those with skill in the art will realize that the invention also applies to other transposons or artificial transposons. Specific EZ::TN Transposons will be designated herein as follows: The term "EZ::TN," which designates an artificial Tn5 transposon having hyperactive ME sequences, is followed by the names of each specific gene within the transposon, each of which is separated from the other by a forward slash (/); then, the names of all of the genes or genetic elements within the transposon are flanked by arrows (< >) which indicate the orientation of the terminal ME sequences; finally, this is followed by the word "Transposon" or "Transposome," as the case may be. For example, an "EZ::TN <oriV/KAN> Transposon" or an "EZ::TN <or V/KAN> Transposome" designates, respectively, an artificial Tn5 transposon or a Transposome™ complex which has the oriV origin of replication and a kanamycin-resistance gene.

As used herein, an "Insertion Reaction" refers to a reaction which results in transposition of a transposon into a target DNA. EZ::TN Transposase can catalyze insertion of an EZ::TN Transposon into any target DNA in vitro.

A "Transposome™" or a "Transposome™ Complex" as used herein means a synaptic complex formed between a transposon and a transposase, which is stable in the absence of magnesium cations, but which can catalyze insertion of the transposon into another DNA following activation by magnesium cations in vitro or in vivo (Goryshin, I Y, et al., "Insertional transposon mutagenesis by electroporation of released Tn5 transposition complexes", Nature Biotechnol., 18, 97, 2000; Hoffman, L M, et al., "In vivo transposition of transposon/transposase complexes into the genome of Saccharomyces," Current Genet., 35, 305, 1999; Hoffman, LM, et al., "Transposome insertional mutagenesis and direct sequencing of microbial genomes," Genetica, 108, 19–24, 2000). A stable EZ::TN Transposome, which can even be stored for long periods in the freezer, is formed by incubating an EZ::TN Transposon and EZ::TN Transposase in the absence of Mg2+. Some EZ::TN Transposomes, such as EZ::TN <KAN-2>Tnp Transposome, are commercially available from EPICENTRE.

By the "Transposomics™ Field," the inventors mean a field constituting the myriad in vitro and in vivo applications of Transposomes, whether the Transposome is used as a stable complex or is formed in situ in an in vitro insertion reaction.

"EZ::TN Insertion Kits" or "Transposon Insertion Kits," as used herein, refer to kits containing reagents and optimized protocols and optionally, controls, for performing in vitro insertion reactions. For example, EZ::TN Insertion Kits for inserting EZ::TN <TET-1> or EZ::TN <KAN-2> Transposons into target DNA in vitro are available from EPICENTRE.

"Transposon Construction Vectors" refer to specially-constructed vectors available from Epicentre for construction of custom EZ::TN Transposons. For example, PMOD™ <MCS> Transposon Construction Vector is a plasmid vector with a multiple cloning site (MCS) between OE Sequences recognized by EZ::TN Transposase.

When used herein, "Deletion/Inversion Vectors" refer to specially-constructed plasmid or cosmid or other circular vectors in which OE sequences are oriented in such a way that transposase-catalyzed transposition results in random unidirectional deletion or inversion of a portion of the DNA that has been cloned into a certain sites on the vector. Examples include the pWEB::TNC™ Cosmid Vector, and pPDM™-1 and pPDM™-2 Deletion Plasmid Vectors.

"Transposon Tools" refers to all kits and reagents which utilize artificial transposons or a transposase.

DETAILED DESCRIPTION OF THE INVENTION

A preferred embodiment of the invention is a method for retrofitting DNA in single-copy or low-copy vectors with the capability of replicating at higher copy number, said method comprising: (a) contacting the DNA in one or more vectors, in vitro or in vivo, with an artificial transposon under conditions which permit insertion of the transposon into the DNA in one or more of these vectors so as to obtain one or more insertion clones, said transposon comprising DNA encoding a conditional or otherwise controllable multi-copy origin of replication ("ori") and optionally comprising one or more selectable markers; (b) introducing DNA from one or more transposon insertion clones into bacterial host cells containing a gene which encodes at least one polypeptide required for replication from the conditional multi-copy ori contained in the transposon, and the expression of which polypeptide requires the presence of at least one inducer molecule; and (c) contacting the host cells containing said transposon insertion clones with an inducer under conditions which result in expression of the polypeptide required by the ori and replication of insertion clones from the multi-copy ori.

In a particularly preferred embodiment of the method for retrofitting DNA in single-copy or low-copy vectors with the capability of replicating at higher copy number, the conditional or otherwise controllable multi-copy origin of replication in said transposon is oriV [SEQ. ID No. 1], which is different from the sequence of the or/V used in U.S. Pat. No. 5,874,259, and the polypeptide required for replication from said conditional multi-copy ori contained in the transposon is an up-copy mutant of the trfA gene under the control of an araB promoter, which trfA gene is expressed in host cells in the presence of L-arabinose.

In one preferred embodiment of the method for retrofitting DNA in single-copy or low-copy vectors with the capability of replicating at higher copy number, the transposon is inserted in vitro in the presence of a transposase enzyme which catalyzes transposition of said transposon under suitable conditions.

In another preferred embodiment of the method for retrofitting DNA in single-copy or low-copy vectors with the capability of replicating at higher copy number, the transposon is inserted in vivo using a Transposome™ complex comprising said transposon and a transposase enzyme which catalyzes transposition of said transposon under suitable conditions.

In another preferred embodiment of the method for retrofitting DNA in single-copy or low-copy vectors with the capability of replicating at higher copy number, the transposon is chosen from among an artificial Tn5-based transposon, such as but not limited to, an EZ::TN™ transposon (EPICENTRE), or another artificial transposon, including, but not limited to, a form of a Tn7 transposon, a Mu transposon, a Mariner transposon, a Tn10 transposon, a Tn552 transposon, or a transposon comprising the T-DNA ends of an *Agrobacterium* Ti- or Ri-plasmid.

Another preferred embodiment of the invention is a kit for retrofitting DNA in single-copy or low-copy vectors with the capability of replicating at higher copy number, said kit comprising one or more of the following: (a) a transposon comprising DNA encoding a conditional or otherwise controllable multi-copy origin of replication ("ori") and optionally comprising one or more selectable markers; (b) host cells containing a gene which encodes at least one polypeptide required for replication from the conditional or otherwise controllable multi-copy ori contained in the transposon, and the expression of which polypeptide requires the presence of at least one inducer molecule; and (c) an inducer, said inducer which, under appropriate conditions, results in expression of the polypeptide required by the ori for replication.

Another preferred embodiment of the invention is a method for cloning DNA that lacks an ori for replication in a particular host cell, said method comprising: (a) contacting said DNA, in vitro, with an artificial transposon under conditions which permit insertion of the transposon into the DNA at one or more sites per DNA molecule, said transposon comprising DNA encoding both a single-copy F-factor replicon or an equivalent single-copy or low-copy ori and a conditional or otherwise controllable multi-copy ori and optionally comprising one or more selectable markers; (b) breaking said DNA into fragments which have a size range from about 500 bp to about 500 kb by random shearing or by digesting with one or more enzymes having nuclease activity; (c) optionally, treating said DNA so as to generate blunt-ended termini; (d) treating said DNA so that the ends of a proportion of said DNA molecules are operably joined so as to form circular DNA molecules by using a chemical or enzymatic composition with joining activity; (e) introducing said DNA containing said transposon insertions into host cells in which the single-copy ori is functional and which host cells contain a gene which encodes a polypeptide required for replication from the conditional multi-copy ori contained in the transposon, and the expression of which polypeptide requires the presence of at least one inducer molecule; and (f) contacting the host cells containing said transposon insertion clones with an inducer under conditions which result in expression of the polypeptide required by the multi-copy ori and replication of insertion clones from the multi-copy ori.

In a particularly preferred embodiment of the method for cloning DNA that lacks an ori for replication in a particular host cell, the conditional or otherwise controllable multi-copy origin of replication in said transposon is oriV [SEQ ID No. 1], which sequence is different from the sequence of the or V used in U.S. Pat. No. 5,874,259, and the polypeptide required for replication from said conditional multi-copy ori contained in the transposon is an up-copy mutant of the trfA gene under the control of an araB promoter, which trfA gene is expressed in host cells in the presence of L-arabinose.

Another preferred embodiment of the invention is a kit for cloning DNA that lacks an ori for replication in a particular host cell, said kit comprising one or more of the following: (a) a transposon comprising DNA encoding both an F-factor replicon or an equivalent single-copy or low copy ori and a conditional or otherwise controllable multi-copy ori and optionally comprising one or more selectable markers; (b) host cells in which the F-factor or equivalent single-copy or low copy replicon is functional and which contain a gene which encodes at least one polypeptide required for replication from the conditional or otherwise controllable multi-copy ori contained in the transposon, and the expression of which polypeptide requires the presence of at least one inducer molecule; and (c) an inducer, said inducer which, under appropriate conditions, results in expression of the polypeptide required by the ori for replication.

Another preferred embodiment of the invention is an improved vector which is capable of conditional amplification to higher copy number under suitable conditions in a suitable host, said vector comprising a DNA molecule comprising the oriV origin of replication [SEQ ID NO. 1]. The DNA molecule comprising oriV SEQ ID NO. 1 in said vector is preferable to and has a sequence that is different from the sequence that was used and disclosed by the inventors in U.S. Pat. No. 5,874,259. Thus, said vector is useful for the methods disclosed in U.S. Pat. No. 5,874,259, as well as in other methods not disclosed therein.

A particularly preferred embodiment of the invention is an improved vector which is capable of conditional amplification to higher copy number under suitable conditions in a suitable host, said vector comprising a DNA molecule comprising the oriV origin of replication [SEQ ID NO. 1] which is operably joined to a DNA molecule comprising pIndigoBAC-5, which vector is constructed by:

a. treating pIndigoBAC-5 with Xho I restriction enzyme so as to generate a linear DNA molecule, and b. treating said Xho I-linearized pIndigoBAC-5 DNA molecule with a T4 DNA polymerase and a T4 polynucleotide kinase in the presence of dNTP nucleotides under suitable conditions so as to generate a blunt-ended and 5'-phosphorylated linear pIndigoBAC-5 DNA molecule; and c. incubating said 5'-phosphorylated linear pIndigoBAC-5 DNA molecule with the DNA molecule comprising oriV in the presence of a ligase under suitable conditions so as to obtain joining of both ends of the DNA molecule comprising oriV to the DNA molecule comprising pIndigoBAC-5

Those with skill in the art will know other ways to make the vector described above. The invention is intended to include the same vector or a substantially similar vector which comprises SEQ ID NO. 1, whether constructed as described herein above or constructed using other methods. Various preparations of this vector are available from EPICENTRE under the names of pCC1, pCC1BAC, and pCC1FOS, as describe in EPICENTRE Technologies' Product Literature, including, for example, Product Literature No. 174 for the CopyControl™ PCR Cloning Kit.

Another preferred embodiment of the invention is a method for constructing a bacterial host strain which, in the presence of an inducer, expresses a protein or polypeptide required for replication from a multi-copy ori, said method comprising in vivo insertion of a gene for said protein or polypeptide into the chromosomal DNA of said bacterium by means of a Transposome™ or synaptic complex between a transposase and an artificial transposon, said transposon comprising a gene for said protein or polypeptide required for replication from said multi-copy ori which is operably joined to an inducible promoter which results in transcription of said gene and expression of said protein or polypeptide under suitable conditions in the presence of said inducer. An E. coli strain is a particularly preferred bacterial strain for this method of the invention. The use of an EZ::TN™ Transposon comprising the trfA gene which is operably joined to an inducible araB promoter, which transposon is used to make an EZ::TN™ Transposome for use in the method, are also particularly preferred embodiments of this method of the invention, in which case the host supports multi-copy replication of a DNA molecule having oriV. Another embodiment of the invention uses an EZ::TN™ Transposon comprising the pir gene which is operably joined to an inducible araB promoter, which transposon is used to make an EZ::TN™ Transposome, in which case the host supports multi-copy replication of a DNA molecule having an R6K(Gamma) ori. Those with skill in the art will know or know how to identify other embodiments of the invention. The invention is not limited to the use of a particular host, transposase, ori, ori-supporting protein or polypeptide or the gene which encodes it, or inducible promoter, and includes all such suitable compositions.

Another preferred embodiment of the invention is a host strain made using this method for constructing a bacterial host strain which, in the presence of an inducer, expresses a protein or polypeptide required for replication from a multi-copy ori. A particular preferred host strain of the invention is the E. coli EPI300™ strain, which was constructed as described in Example I(A) herein below.

Additional embodiments of the invention will be obvious to those with skill in the art by reading the remaining detailed description of the invention and the examples herein.

The inventors addressed the use of transposons to deliver a conditional ori into BACs in vivo in order to permit amplification of BAC DNA in the host cell, thus reducing the culture volumes necessary to purify sufficient BAC DNA for sequencing. Using a novel Tn5-based transposon insertion technology, an artificial transposon having a conditional origin of replication, selectable marker and primer binding sites sequencing was inserted into BAC clones. Use of this transposon strategy provides the following technical benefits: (1) primer binding sites on the transposon are inserted randomly into the BAC, permitting bi-directional sequencing from each insertion site; (2) the need to purify BAC DNA clones and sub-clone them into "shatter" clones for sequencing is eliminated; and (3) the copy numbers of BAC insertion clones are increased in host cells that support multi-copy replication from the conditional origin of replication, thereby generating higher quantities of BAC DNA template for sequencing, and enabling use of automated high-throughput procedures.

It is known that when the R6Kγ ori is present in a plasmid, its copy number is dependent on Π (Pi) Protein in the host cell. In order to test the feasibility of using this system to increase the quantity of DNA for sequencing of insertion clones, a transposon was constructed that had an R6Kγ ori. This Tn5-based artificial transposon contained 19-bp outer ends, the R6Kγ origin of replication (ori), a selectable marker, and primer binding sites for sequencing. Then, the R6Kγ ori-containing transposon was used to make random insertions into BAC clones in living E. coli cells using a novel in vivo Transposome™ strategy. Using this strategy, up to thousands of transposon insertion clones were obtained for each BAC clone following electroporation of an antibiotic-resistant Transposome (the complex between an artificial transposon and EZ::TN™ Transposase) into electrocompetent E. coli containing the BAC clone of interest. A single transposon was randomly inserted into each BAC insertion clone. The results were encouraging. BAC clones up to 100 kb were amplified >10-fold in E. coli strain EC100D™ pir+, which produces Π protein that induces the R6Kγ ori to 15–20 copies per cell. However, BAC clones of 150 or 200 kb were unstable and could not be amplified in strain EC100D pir+ and none of the sizes of BAC clones, including 100-kb clones, was stable in E. coli strain EC100D™ pir-116, which is capable of inducing the R6Kγ ori to about 250 copies per cell. Thus, the stability of the insertion clones in E. coli cells constitutively expressing Π Protein varied depending on the size of the clone. These experimental results demonstrated the feasibility of using a controllable ori, but indicated a need to develop a system to regulate the number of BACs present in a cell "at will" in a manner that was not size-dependent. The limitations of the constitutively expressed R6Kγ ori system led the inventors to use inducible ori's as a means of more precisely controlling BAC copy number and enhancing the probability of success in amplifying large BAC clones.

When BAC insertion clones were used to transform different electrocompetent E. coli host strains that constitutively expressed Pi Protein, the copy numbers of BAC insertion clones up to about 100 kb were amplified >10fold in an E. coli host strain that expressed Pi Protein that theoretically would support a copy number of 15–25 copies of the R6Kγ ori per cell. These results demonstrated that transposons containing a conditional ori can be used to increase the copy number and DNA yield of BAC clones. Modifying pir-containing E. coli strains so that the wild-type or a mutant pir gene is under the control of an inducible promoter provides a means for at-will control of copy number for vectors containing an R6Kγ ori.

EXAMPLES

Example I

Construction of Bacterial Strains

New E. coli host strains comprising at least one polypeptide required for replication from a conditional origin of replication were constructed using E. coli strain Transfor- Max™ EC100™ (F— mcrA Δ[mrr-hsdRMS-mcrBC] 80dlacZΔM15 ΔlacX74 recA1 endA1 araD139 Δ(ara, leu) 7697 galU galK λ-rpsL nupG), which is commercially available from EPICENTRE.

A. Construction of the *E. coli* EPI 300™ strain which expresses a mutant Form of the TrfA Protein Under the Control of the Arab Promoter

*E. coli* strain JW366, which contains a mutant trfA gene under the transcriptional control of the P(sub)BAD promoter and the regulatory protein araC, was obtained from Professor Waclaw Szybalski, University of Wisconsin-Madison under a license agreement for U.S. Pat. No. 5,874,259 and related patent applications. A blunt-ended DNA fragment comprising the AraC, the P(sub)BAD promoter and the trfA gene (hereinafter referred to as the "trfA cassette") was first recovered from chromosomal DNA of strain JW366 by PCR using the FailSafe™ PCR System and primers with the following sequences: Forward: 5'-TTATGACAACT-TGACGGCTACATC-3' [Sequence I.D. No. 2]; and Reverse: 5'-CCTAGCGTTTGCAATGCACCA-3' [Sequence I.D. No. 3]. Then, a DNA molecule comprising the EZ::TN™ <DHFR-1> Transposon, either as a linear DNA molecule (commercially available as a purified transposon from EPICENTRE) or on a plasmid, is digested using Kpn I restriction enzyme. The Kpn I ends are made blunt-ended using the End-It™ DNA End-Repair Kit (EPICENTRE) according to the protocol of the manufacturer, and ligated to the blunt-ended trfA cassette. An artificial Tn5-based transposon containing the trfA cassette is then prepared by Pvu II digestion using a protocol similar to one of the methods described for preparing EZ::TN™ Transposons in Product Literature No. 145 for the EZ::TN™ pMOD™-2<MCS> Transposon Construction Vector (EPICENTRE). The resulting transposon is used to prepare Transposome™ complexes as described in the same Product Literature No. 145. Thousands of random insertion clones were obtained following electroporation of the Transposomes into TransforMax™ EC100™ Electrocompetent *E. coli* cells and selection on trimethoprim-containing medium. Some of the insertion clones were then chosen for additional analysis by sequencing outward from the transposon using transposon-homologous primers in order to identify the chromosomal insertion site. Some of these were also analyzed for their ability to support multi-copy replication of an oriV-containing plasmid. One insertion clone, designated as the "EPI300™ strain", was found to have the desired properties of improved transformation efficiency by electroporation and good induction of oriV-containing vectors and of oriV-containing clones to higher copy number for clones with a broad range of insert sizes. The chromosomal insertion site of the trfA cassette-containing transposon in the EPI300™ strain was identified as a site within the dpm I gene. The dpm I gene appears to be a homolog of eukaryotic dolichol-phosphate mannose synthase, a mannose transferase, which may be involved in carrier lipid formation in bacterial cell wall synthesis, although very little is known about the role or roles of dolichol-phosphate mannose synthase in bacterial cell wall synthesis; thus, the nature or role of the insertion site should not be interpreted so as to limit the invention. Strains in which the trfA cassette is inserted in other chromosomal locations are also suitable for use in the invention provided that such strains yield similar transformation efficiencies to the EPI300 strain and are able to support replication of oriV-containing vectors with inserts having a broad range of clone insert sizes, and so long as the insertion into the chromosomal DNA of the host strain does not result in other detrimental effects.

B. Construction of *E. coli* Strains Which Express Pi Protein

*E. coli* strains which express different constitutive levels of the pi Protein, a product of the pir gene which is required for replication of DNA from the R6Kγ ori, were constructed for use with vectors having the R6Kγ ori. Each pir-containing strain of *E. coli* was constructed using similar methods. *E. coli* strains BW19612 and BW19610 containing either the pir+ gene or pir-116 gene (Metcalf, W., et al., "Use of the rep technique for allele replacement to construct new *Escherichia coli* host for maintenance of R6K(gamma) origin plasmids at different copy numbers," Gene, 138, 1–7, 1994), respectively, were transformed with a Transposome™ containing the dihydrofolate reductase gene (conferring Trimethprim resistance on a cell) by electroporation. Trimethoprim-resistant cells were infected with phage P1, generating a P1 library containing the DNA from the transposon-containing *E. coli*. The P1 library was used to infect *E. coli* EC100™ cells and the resulting transductants were screened for trimethoprim resistance and ability to permit growth of a plasmid with the R6Kγ ori. The resulting genotype of EC100D pir+ is (F-mcrA Δ[mrr-hsdRMS-mcrBC] φ80dlacZΔM15 ΔlacX74 recA1 endA1 araD139 Δ(ara, leu)7697 galU galK λ-rpsL nupG pir+(DHFR). Similarly, *E. coli* EC100D pir-116 was constructed by P1 transduction of *E. coli* EC100 cells with DNA from a second *E. coli* strain containing the mutant pi gene linked to the dihydrofolate reductase gene. Both strains are now commercially available from EPICENTRE.

Example II

Nucleic Acids

BAC-1 is a 100 kb BAC containing human DNA inserted into pBeloBAC-11. BAC-2 is a 150 kb BAC clone of human DNA in pBeloBAC-11. Both of these BACs were generously provided to EPICENTRE by Dr. Hiroake Shizuya of California Institute of Technology. BAC-3 is a 200 kb clone of human chromosome 7q21-1 through 7q21-3 from the short arm of Chromosome 7 (GenBank accession number HGS286B23), and was purchased from Genome Systems, Inc. (St. Louis, Mo.). The PMOD™ Transposon Construction Vector is a 2.7 kb plasmid containing the mosaic ends of the hyperactive Tn5 transposon, the ColE1 ori, an ampicillin resistance gene and a multiple cloning site.

A. Construction and Analysis of an Improved Vector Containing an oriV Origin of Replication In order to obtain a vector with single-copy clone stability and improved performance compared to other vectors obtained under a license agreement in terms consistent on-demand inducibility of clone copy number for a continuous range of clone sizes, from less than one kb up to greater than 150 kb, a vector containing an oriV conditional origin of replication was constructed as follows: Circular pIndigo-BAC-5™ Vector, which is commercially available from EPICENTRE, was linearized at the unique Xho I site in the vector. The Xho I ends were then made blunt-ended using the End-It™ DNA End-Repair Kit (EPICENTRE) according to the protocol of the manufacturer. Finally, this blunt-ended vector was ligated to a blunt-ended 618-basepair DNA fragment comprising oriV [Sequence I.D. No. 1]; this sequence is different from the sequence for oriV disclosed in U.S. Pat. No. 5,874,259. Cloning-ready forms of this vector are commercially available from EPICENTRE under the pCC1™, pCC1 BAC™, and pCC1 FOS trademarked names.

Following transformation of TransforMax™ EC100™ or TransforMax™ EPI300™ electrocompetent *E. coli* with pCC™1, the vector replicates at approximately one copy per cell in the absence of inducer. However, when cells containing pCC™-1 are grown in the presence of L-arabinose inducer (as described in EPICENTRE Technologies' Product Literature No. 176 for the CopyControl™ Induction Solution), the pCC1 vector in TransforMax EPI300 cells increases to approximately 50 copies per cell. The pCC1 vector in TransforMax EC100 cells, which do not contain an inducible trfA gene, continues to replicate at approximately one copy per cell (presumably from the F-factor replicon).

Clones of PCR products ranging from less than 500 basepairs to about 5 kb, approximately 40-kb fosmid clones, and BAC clones up to greater than 150 kb all grew at approximately one copy per cell in uninduced TransforMax EPI300 cells, but the copy numbers of all of these kinds and sizes of clones increased to approximately 10–50 copies per cell following induction with L-arabinose. Thus, a 1-ml culture of an induce BAC clone typically yields sufficient DNA for sequencing and fingerprinting, making high throughput applications easier and more feasible. Since the proportion of BAC DNA to chromosomal DNA is higher, it is also easier to obtain DNA of higher purity for use in sequencing and other applications. At a single copy, all of the clones examined, including BAC clones up to about 200 kb appear to be genetically stable over time based on gel analysis of restriction fingerprints. It also appears that more clones are obtained when total prokaryotic chromosomal DNA, cDNA, or PCR products are cloned at single copy compared to the same DNA cloned at multi-copy per cell. Without limiting the invention, the inventors believe that one explanation for this would be that certain clones are more viable for the host cell at single copy than at multi-copy. For example, genes which express toxic or detrimental gene products might be more tolerated at single copy than at multi-copy. Also, for whatever reason, some sequences, such as repetitive sequences and possibly AT-rich and GC-rich sequences, appear to be more difficult to clone. The inventors believe that it may be more likely to clone such difficult-to-clone sequences at single-copy in the inducible ori vectors of the invention, yet permit induction to high copy number on-demand in order to obtain a greater quantity of DNA for analysis and other applications.

B. Construction and Analysis of an Artificial Tn5-Based Transposon Containing the oriV Conditional ori and Construction of the Corresponding Transposome™ Complex.

An artificial Tn5-based transposon containing oriV was constructed as follows: The KAN-2 kanamycin resistance gene described above was first cloned into the MCS of the pMOD™-2<MCS> Transposon Construction Vector. Following transformation of TransforMax™ EC100™ Electrocompetent *E. coli* cells (EPICENTRE) and purification of the plasmid from cultures of a single colony, the resulting recombinant product was linearized at the unique Hinc II site and ligated to a blunt-ended 618-basepair DNA fragment comprising oriV [Sequence I.D. No. 1]. The oriV-containing transposon and corresponding Transposome™ complexes are prepared as described in the Product Literature No. 145 for the EZ::TN™ pMOD™-2<MCS> Transposon Construction Vector (EPICENTRE), incorporated herein by reference, and in vitro and in vivo insertion reactions were performed according to conditions similar to those described therein. Using these methods, both an EZ::TN <oriV/KAN-2> Transposon and an EZ::TN <oriV/KAN-2> Transposome complex were obtained.

The EZ::TN <oriV/KAN-2> Transposon and the EZ::TN <oriV/KAN-2> Transposome complex both functioned effectively for retrofitting clones to high copy number. Thus, thousands of oriV-containing transposon insertion clones are typically generated in vitro or in vivo by the transposon or Transposome, respectively. Once inserted into BAC, fosmid, or plasmid clones or vectors, most of the resulting insertions clones appear to be stable at single copy over time based on gel analysis of restriction enzyme fingerprinting and the insertion clones are stably maintained at approximately one copy per cell in TransforMax™ EC100™ cells or in uninduced TransforMax™ EPI300™ cells. However, insertion clones can be induced to 10–50 or more copies per cell in TransforMax™ EPI300™ cells by addition of an appropriate amount of L-arabinose to well-aerated culture medium. An additional benefit of the method for using insertion clones for retrofitting single-copy or low-copy vectors to higher copy number is that the clone DNA can be sequenced in both direction from the various random insertion sites using only primers that are homologous to each end of the transposon. Thus, the complete sequence of any clone that is too large to sequence with a single set of sequencing reactions (whether 1 kb or 200 kb) can be determined quickly and easily by sequencing a collection of random insertion clones.

C. Construction of an Artificial Tn5-Based Transposon Containing the R6Kγ Conditional ori and Construction of the Corresponding Transposome™ Complex.

The R6Kγ ori-containing artificial Tn5-based transposon was constructed as follows: The DNA molecule comprising the R6Kγ ori was ligated to the KAN-2 kanamycin resistance gene which is present in the EZ::TN™ <KAN-2> Transposon (EPICENTRE). This cassette was then cloned into the multiple cloning site (MCS) of the pMOD™-2 <MCS> Transposon Construction Vector (EPICENTRE) to obtain the EZ::TN™ <R6Kγori/KAN-2> Transposon, which is now commercially available from EPICENTRE. The corresponding Transposome™ complex, which is also commercially available in the EZ::TN™ <R6Kγori/KAN-2>Tnp Transposome™ Kit (EPICENTRE), was prepared as described "For Production of Transposomes" in the Product Literature No. 169 for the EZ::TN™ pMOD™-3<R6Kγori/ MCS> Transposon Construction Vector (EPICENTRE), incorporated herein by reference.

D. Construction of R6Kγori-Containing BACs

The EZ::TN <R6Kγori/KAN-2> Transposome™ (EPICENTRE) was used to randomly insert the conditional *E. coli* R6Kγ origin of replication (R6Kγ ori) into BAC target DNA in vivo as described in EPICENTRE Technologies' Product Literature No. 155, incorporated herein by reference.

E. Electroporation of Host Cells: Example Using BAC-1, BAC-2 and BAC-3

An aliquot of the Transposome™ was placed into a 2 mm gapped cuvette of an Eppendorf electroporator, along with 50 μl of *E. coli* EC100™ (EPICENTRE) containing either BAC-1, BAC-2 or BAC-3 and transformed at 2500 volts for 5 milliseconds. The transformants were placed into 1 ml of LB medium and permitted to recover for 1 h. Aliquots of the transformed cell lines were plated on LB plates containing kanamycin at 50 μg/ml, and incubated at 37° C. for 24 hr. Colonies from an entire plate were harvested in an "orgy" preparation. BAC DNA was isolated, quantified and transformed into TransforMax™ EC100™, TransforMax™ EC100D™ pir+, or TransforMax™ EC100D™ pir-116 Electrocompetent E. coli cells (EPICENTRE).

F. Recovery and Quantitation of BAC DNA Following In Vivo Transposon Insertion Using an EZ::TN <R6Kγori/KAN-2> Transposome™ Complex BAC DNA was harvested from each plate and analyzed for copy number and for deletions in the BACs using colony screening reagents and agarose gel electrophoresis.

Transposed BAC-containing cells (chloramphenicol and kanamycin-resistant colonies) were counted to determine the number of random insertions into each BAC, and to quantify the amount of BAC DNA present in each of the host cell/BAC clone combinations.

G. Clone Stability and Copy Number of EZ::TN <R6Kγ ori/KAN-2> Insertion Clones of BACs of Varying Size in E. coli Strains Expressing Different Constitutive Levels of a Mutant Pi Protein

| BAC | Host cell | BAC size | Copy # | Stability | Mutations & deletions |
|---|---|---|---|---|---|
| BAC-1 | EC100 pir– | 100 kb | 1–2 | Stable | None |
| BAC-1 | EC100 pir+ | 100 kb | 10–15 | Stable | None |
| BAC-1 | EC100 pir–116 | 100 kb | UD* | Not Stable | Many |
| BAC-2 | EC100 pir– | 150 kb | 1–2 | Stable | None |
| BAC-2 | EC100 pir+ | 150 kb | 10** | Less stable | Few |
| BAC-2 | EC100 pir–116 | 150 kb | UD | Not Stable | Many |
| BAC-3 | EC100 pir– | 200 kb | 1–2 | Stable | None |
| BAC-3 | EC100 pir+ | 200 kb | UD | Not Stable | Many |
| BAC-3 | EC100 pir–116 | 200 kb | UD | Not Stable | Many |

*UD = Unable to determine
**Approximately 75% of amplified 150 kb BAC-2 were stable in the host cell.

The data tabulated above indicate that there is a size bias for amplifying BAC DNA in host cells that is dependent on the status of the pir gene product in the E. coli host cells. In E. coli EC100™, which lacks Pi Protein (pir-minus), all three BAC species were maintained at 1–2 copies per cell without obvious deletions or mutations.

Host strain EC100D™ pir+was able to maintain BAC-1 (100 kb) in a stable manner at a level of 10 BACs per cell. With BAC-2 (150 kb), BAC stability was reduced, and many of the BACs assayed had deletions. Two colony types were noted: large colonies tended to yield BACs that had deletions; small colonies contained fewer BACs, but tended to yield apparently intact BACs. BAC-3 (200 kb) produced 100-fold less colonies that contained BAC DNA, and those colonies that did contain BACs were not amplifiable when isolated and re-transformed into pir+ hosts.

Host strain EC100D™ pir-116 was not able to maintain BAC DNA in stable fashion when tested with any of the three BACs. This strain, containing the up-copy number variant pir gene in the E. coli host, is theoretically able to maintain episomal DNA at 100–200 copies per cell. The inventors found that, in the pir-116 hosts that did retain a BAC, the BAC had deletions and were not stable in the cell. BACs recovered from these hosts and retransformed into the same pir-116 strain could no longer be amplified.

The instability of large (150 Kb) BAC DNA in EC100D™ pir+ and EC100D™pir-116 strains precluded meaningful sequencing of DNA with transposons containing the R6Kγ ori and led us to consider other methods for regulating activation of the R6Kγ ori or other conditional ori's. The amount of BAC DNA synthesized during replication from the R6Kγ ori is dependent upon the amount of pir gene product, which was constitutively expressed in these hosts. This led the inventors to explore other regulatory genes and how they are expressed as an alternative means of controlling BAC populations or copy number within a host. Without limiting the invention, it was speculated that inducible genes, which are well known in molecular biology, may be useful shifting BAC synthesis in a host to a later point in the cell's life cycle, where cell growth in culture is largely complete.

All publications and patents mentioned in the above specification are herein incorporated by reference. Various modifications and variations of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, protein fermentation, biochemistry, or related fields are intended to be within the scope of the following claims.

What is claimed is:

1. A host constructed using a method for constructing a bacterial host strain which, in the presence of an inducer, expresses a protein or polypeptide required for replication from a multi-copy ori, said method comprising in vivo insertion of a gene for said protein or polypeptide required for replication from a multi-copy ori into the chromosomal DNA of bacterial host by means of a synaptic complex between a transposase and an artificial transposon, said transposon comprising a gene encoding said protein or polypeptide required for replication from said multi-copy ori which is operably joined to an inducible promoter which results in, transcription of said gene and expression of said protein or polypeptide under suitable conditions in the presence of an inducer of said inducible promoter, wherein said artificial transposon comprises an artificial Tn5 transposon comprising hyperactive Mosaic End (ME) sequences and a trfA gene which is operably joined to an inducible araB promoter.

2. A bacterial host strain which, in the presence of L-arabinose, expresses the trfA Protein required for replication from an oriV origin of replication, said bacterial host strain comprising a trfA gene inserted in the chromosomal DNA of said bacterial host strain, wherein said trfA gene is operably joined to an araB promoter which results in transcription of said trfA gene and expression of said trfA Protein under suitable conditions in the presence of L-arabinose and wherein the inserted trfA gene is flanked by two 19-basepair ME sequences of a hyperactive Tn5 transposon.

3. The bacterial host strain of claim 2 wherein the trfA gene is inserted in a dpm1 gene.

4. The bacterial host strain of claim 2 wherein the bacterial host strain, in the presence of L-arabinose, expresses the TrfA Protein required for replication from an oriV origin of replication comprising SEQ ID No. 1.

* * * * *

SEQUENCE LISTING

<160> NUMBER OF SEQ ID NOS: 3

<210> SEQ ID NO 1
<211> LENGTH: 618
<212> TYPE: DNA
<213> ORGANISM: Artificial Sequence
<220> FEATURE:
<223> OTHER INFORMATION: Description of Artificial Sequence: oriV
      derived from a commercial vector

<400> SEQUENCE: 1
gctggttgcc ctcgccgctg ggctggcggc cgtctatggc cctgcaaacg cgccagaaac      60
gccgtcgaag ccgtgtgcga gacaccgcgg ccggccgccg gcgttgtgga tacctcgcgg     120
aaaacttggc cctcactgac agatgagggg cggacgttga cacttgaggg gccgactcac     180
ccggcgcggc gttgacagat gaggggcagg ctcgatttcg gccggcgacg tggagctggc     240

```
                                    -continued cagcctcgca aatcggcgaa aacgcctgat tttacgcgag tttcccacag atgatgtgga      300
caagcctggg gataagtgcc ctgcggtatt gacacttgag gggcgcgact actgacagat      360 gagggggcgcg atccttgaca cttgaggggc agagtgctga cagatgaggg gcgcacctat     420
tgacatttga ggggctgtcc acaggcagaa aatccagcat ttgcaagggt ttccgcccgt      480
ttttcggcca ccgctaacct gtcttttaac ctgcttttaa accaatattt ataaaccttg      540
tttttaacca gggctgcgcc ctgtgcgcgt gaccgcgcac gccgaagggg ggtgccccc      600 cttctcgaac cctcccgg                                                    618

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 2
ttatgacaac ttgacggcta catc                                             24

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 3
cctagcgttt gcaatgcacc a                                                21
```